United States Patent [19]

Perez-Soler et al.

[11] Patent Number: 4,863,739
[45] Date of Patent: Sep. 5, 1989

[54] LIPOSOME COMPOSITIONS OF ANTHRACYCLINE DERIVATIVES

[75] Inventors: Roman Perez-Soler; Waldemar Priebe; Gabriel Lopez-Berestein, all of Houston, Tex.

[73] Assignee: Board of Regents, The University of Texas System, Austin, Tex.

[21] Appl. No.: 51,890

[22] Filed: May 19, 1987

[51] Int. Cl.$^4$ .................. A61K 37/22; A61K 9/66; A61K 45/05; B01J 13/02

[52] U.S. Cl. .................. 424/450; 264/4.3; 264/4.6; 428/402.2; 436/829; 514/34; 514/908

[58] Field of Search .................. 264/4.3, 4.6; 428/402.2; 424/450; 436/829; 514/908, 34

[56] References Cited

U.S. PATENT DOCUMENTS

| | | | |
|---|---|---|---|
| 3,590,028 | 6/1971 | Arcamone et al. | 536/6.4 |
| 3,803,124 | 4/1974 | Arcamone et al. | 536/6.4 |
| 3,970,641 | 7/1976 | Jolles et al. | 536/6.4 |
| 3,988,315 | 10/1976 | Umezawa et al. | 536/6.4 |
| 3,993,754 | 11/1976 | Rahman et al. | 514/12 |
| 4,031,211 | 6/1977 | Patelli et al. | 514/34 |
| 4,035,566 | 7/1977 | Israel et al. | 536/6.4 |
| 4,201,773 | 5/1980 | Horton et al. | 514/34 |
| 4,229,360 | 10/1980 | Schneider et al. | 260/403 |
| 4,247,411 | 1/1981 | Vanlerberghe et al. | 264/4.3 |
| 4,351,937 | 9/1982 | Stefanska et al. | 536/6.4 |
| 4,419,348 | 12/1983 | Rahman et al. | 514/34 |
| 4,460,577 | 7/1984 | Moro et al. | 424/180 |
| 4,515,736 | 5/1985 | Deamer | 264/4.3 |
| 4,529,561 | 7/1985 | Hunt et al. | 264/4.3 |
| 4,537,882 | 8/1985 | Horton et al. | 514/34 |
| 4,684,629 | 8/1987 | Bargiotti et al. | 514/34 |

FOREIGN PATENT DOCUMENTS

| | | |
|---|---|---|
| 0116222 | 8/1984 | European Pat. Off. |
| 0198765 | 10/1986 | European Pat. Off. |
| 0219922 | 4/1987 | European Pat. Off. |
| WO8400968 | 3/1985 | PCT Int'l Appl. |

OTHER PUBLICATIONS

Horton et al. The Journal of Antibiotics, p. 853, Aug. 1984.
The Merck index, entry numbers 3428 and 2815, (1976).
Dialog search, Search II.
International Search Report.
Perez–Soler et al. (1986), *Cancer Research*, 46:6269–6273.
Ganaphathi et al. (1984), *Biochem. Pharmacol*, 33:698–700.
Olson et al. (1982), *Eur. J. Cancer Clin. Oncol.*, 18:167–176.

*Primary Examiner*—Richard D. Lovering
*Attorney, Agent, or Firm*—Arnold, White & Durkee

[57] ABSTRACT

Disclosed are liposomal antitumor compositions having improved pharmacological characteristics. Liposomes described herein are formed through the incorporation of a particular class of anthracyclines, the 4-demethoxy-3'-desamino-2'-iodo analogs, shown to have extremely high incorporatio efficiencies of greater than 95%. These liposomes demonstrate an improved antitumor efficacy, with much reduced toxicity, against accepted tumor models, and further exhibit excellent stability upon storage, for example, in the form of a dried powder.

22 Claims, No Drawings

LIPOSOME COMPOSITIONS OF ANTHRACYCLINE DERIVATIVES

BACKGROUND OF THE INVENTION

1. Field of the Invention

The present invention relates to liposome incorporated anthracycline derivatives and their use in pharmaceutical compositions for the treatment of cancer.

2. Description of the Related Art

Anthracyclines are a group of antibiotics which have shown significant antitumor activity against several types of human tumors. The most widely used anthracycline, doxorubicin (adriamycin) is a natural product produced by bacteria. Doxorubicin is used as front line therapy against human leukemia, lymphoma, and disseminated human solid tumors (breast, lung, GI, ovary, testicle, etc.). Unfortunately, the use of doxorubicin is severely limited by acute and chronic side effects. Acute side effects such as myelotoxicity limit the amount of doxorubicin that can be administered at one time to a patient. Chronic side effects such as cardiotoxicity limit the use of doxorubicin beyond a cumulative dose of 550 mg/m sq.

During the last decade, a number of anthracyclines have been synthesized in an attempt to decrease the above mentioned side effects. However, none of the analogues that were selected for further development was shown to be clearly superior to doxorubicin in the clinic. Very promising analogues were, however, never selected for preclinical development and fully evaluated in part due to formulation problems in aqueous solutions.

an alternative approach that has been attempted in an effort to improve the pharmacological properties of anthracycline antibiotics is the use of drug carrier techniques such as liposome incorporation. Liposomes are lipid vesicles that form spontaneously upon addition of aqueous solutions to a dry lipid film. Liposomes may entrap drugs in their hydrophilic or lipophilic compartments. Liposomes target mainly to the organs rich in reticuloendothelial system cells although they may also deliver drugs to different types of tumors, specially tumors that involve or arise in these organs.

Liposomes have been employed as carriers of doxorubicin. Incorporation of doxorubicin in liposomes was found generally to result in lower cardiac drug levels, and in a significantly deceased cardiotoxic potential. Unfortunately, all liposomal-anthracycline preparations developed so far have exhibited a low encapsulation efficiency and a poor stability because doxorubicin tends to leak out of the vesicles. Moreover, encapsulation and stability is generally not improved by changing the composition of the liposomes used. These negative characteristics have prevented the wide use of liposomal-doxorubicin in the clinic as a way to decrease the cardiotoxicity of the drug and increase its efficacy against certain types of tumors which are a natural target for liposomes, for example, tumors of monocyte/macrophage lineage and liver metastases of gastrointestinal malignancies.

Due to the importance of anthracycline therapy in the treatment of cancer, there is a continuing need to identify anthracycline derivatives that may be stably incorporated into liposomes in a high enough efficiency to provide novel compositions useful in the treatment of cancer. Additionally, there is a need to provide anthracycline containing compositions having improved antitumor characteristics, including an improved antitumor spectrum, bioavailability and distribution, as well as an improved cardiotoxicity. Unfortunately, these needs have generally gone unfulfilled.

SUMMARY OF THE INVENTION

It is therefore an object of the present invention to address at least some of these and other disadvantages in the art by providing lipid-anthracycline compositions with improved pharmacological characteristics. In general, the present invention embodies the discovery that a certain class of anthracyclines, the 4-demethoxy-3'-desamino-2'-iodo analogs, may be stably encapsulated at high efficacies into liposomal vesicles to provide highly effective antitumor compositions. While these anthracycline derivatives themselves are much too lipophilic to be of use clinically, when liposome-incorporated they may be administered by conventional parenteral routes and are generally much less toxic and better tolerated than doxorubicin.

In certain embodiments, the 4-demethoxy-3'-desamino-2'-iodo anthracyclines of the present invention may be characterized by anthracyclines having the formula:

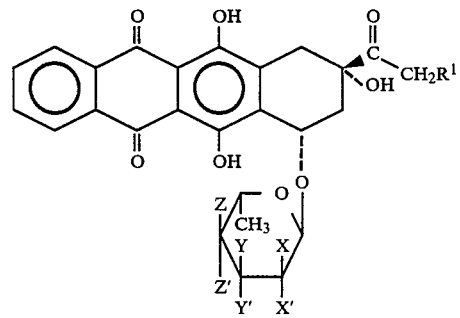

wherein $R^1$ is hydroxy; one of X and X' is hydrogen and the other is iodine; one of Y and Y' is hydrogen and the other is hydroxy; and one of Z and Z' is hydrogen and the other is hydroxy.

In a preferred embodiment, the invention is directed to liposomes having encapsulated therein the antitumor agent (7S,9S)-4-demethoxy-7-O-(2,6-dideoxy-2-iodo-alphamannopyranosyl) adriamycinone (4-DMD), a synthetic anthracycline having the formula:

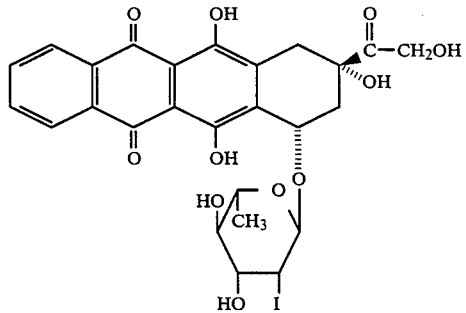

Liposomes of the present invention preferably contain the selected anthracycline in a drug to lipid ratio between about 1 to 5 and 1 to 50, with a more preferred ratio being about 1 to 15. Liposomes comprise phospholipids and cholesterol optionally. Preferred phospholipids include phosphatidylglycerol, phosphatidylcholine, sphingomyelin, phosphatidic acid or phosphatidylserine, the more preferred being phosphatidylglycerol, phosphatidylcholine, or a combination thereof. The most preferred phosphatidylglycerol is one consisting essentially of dimyristoylphosphatidylglycerol and the most preferred phosphatidylcholine is one consisting essentially of dimyristoylphosphatidylcholine.

When the liposomes of the present invention comprise dimiristoylphosphatidylglycerol and dimyristoylphosphatidylcholine they are preferably in a ratio between about 1 to 10 and 10 to 1, more preferably in a ratio of about 3 to 7.

The liposomes may be multilamellar, unilamellar or have an undefined lamellar structure. They may be prepared in a suspension form or may be formed upon reconstitution of a lyophilized powder containing the anthracycline-lipid composition with an aqueous solution. These liposomes of course may be used for the therapy of diseases such as cancer.

An important aspect of the present invention involves a method of treating a host animal afflicted with tumor cells sensitive to the selected anthracycline-liposome composition. This method comprises administering to the host a tumor cell inhibiting effective amount of the selected composition. The administering step is preferably parenteral by intravenous, intraarterial, intramuscular, intralymphatic, intraperitoneal, subcutaneous, intrapleural, or intrathecal injection, or by topical application, or oral dosage. Such administration is preferably repeated following different time schedules. The treatment may be maintained until partial or complete tumor regression has been achieved and may be used in conjunction with other forms of tumor therapy such as surgery, radiotherapy, or chemotherapy with other antitumor agents.

DETAILED DESCRIPTION OF THE PREFERRED EMBODIMENTS

The present invention relates to a particular class of anthracycline derivatives, termed the 4-demethoxy-3'-desamino-2'-iodo anthracyclines, which, in contrast to doxorubicin and other known anthracyclines, can be incorporated into liposomal vesicles at a surprisingly high efficiency. For example, 4-DMD, a prototype member of the class, is found to be stably incorporated into liposomes at efficiencies of 95% or better. These liposomes are stable in that they retain incorporated drugs of this class without leakage upon prolonged storage, as either a liposomal suspension or dried powder. Conversely, doxorubicin is typically incorporated at efficiencies of only 30 to 50%, a level generally found to be inadequate to provide a pharmaceutically acceptable antitumor composition. Moreover, doxorubicin is not stably retained by the liposomes. Thus, the invention, in the most general and overall scope, provides novel antitumor compositions comprised of lipid vesicles having included within a selected 4-demethoxy-3'-desamino-2'-iodo anthracycline.

This class of anthracyclines have been previously described in U.S. Pat. No. 4,537,882, incorporated herein by reference. However, it was discovered by the present inventors that these agents could not be employed clinically in their free form due to a complete lack of solubility in water or other common diluents for parenteral administration. Accordingly, these compounds were found to be virtually useless in the treatment of cancer.

The present invention addresses these and other problems associated with anthracycline therapy in general, and the 4-demethoxy-3'-desamino-2'-iodo derivatives in particular, by providing such agents in a dosage form which allows for their ready parenteral administration. Liposomes of the present invention exhibit extremely high antitumor activity and may be administered by any acceptable parenteral route. Furthermore, these anthracyclines provide a highly uniformally incorporated liposome population with very good storage characteristics.

The use of these specific anthracyclines incorporated in liposomes for the treatment of cancer is described herein as a new effective therapeutic method particularly useful for treatment of tumors that involve or arise in organs such as liver, spleen, lung, bone marrow and lymph nodes. For example, liposome-incorporated 4-DMD has a lowered systemic toxicity and an enhanced therapeutic efficacy as compared to doxorubicin.

Although free-4-DMD exhibits antitumor activity in vitro, it was incapable of being administered parenterally by conventional modes. A reduced in vivo toxicity was observed with liposomal 4-DMD (L-4-DMD), while the antitumor properties were maintained. In vivo, L-4-DMD was found to be much less toxic than doxorubicin, with an $LD_{10}$ of greater than 25 mg/kg versus an $LD_{50}$ of 22 mg/kg for doxorubicin. Moreover, L-4-DMD at 12.5 mg drug/kg body weight was effective in curing 80% of leukemia bearing mice while a roughly equivalent dose of doxorubicin did not result in any cures. Also, L-4-DMD was much more effective than doxorubicin in the treatment of liver metastases of reticulosarcoma.

The most important aspect of the present invention involves liposomes comprising fatty substances such as phospholipids (pl), optionally cholesterol, and the selected 4-demethoxy-3'-desamino-2'-iodo anthracycline, as well as the preparation and uses of these liposomes. Liposomes of the present invention comprise the anthracycline analog and the phospholipid in a preferred anthracycline/pl weight ratio between about 1:5 and about 1:50, a more preferred ratio being between about 1:15. The anthracycline may be part of the phospholipid lamellae, part of the incorporated intraliposomal fluid or both.

As noted, the particular anthracycline analogs embraced by the present invention exhibit surprising incorporation efficiency, typically on the order of or greater than 95%, which render them particular useful as a liposomal anthracycline. Through experiments conducted by the present inventors, it has been observed that certain structural features appear to account for this improved incorporation efficiency to a much more significant degree than indicators typically employed in the art such as lipophilicity. For example, it is believed that the 4-demethoxy-3'-desamino-2'-iodo characteristics themselves are at least a significant consideration. This is due to the observation that anthracyclines having a 4-methoxy and/or 3'-amino tend to be poorly incorporated.

Such liposomes are typically administered parenterally, this route being preferred for anthracycline therapy. Effective parenteral dosages of L-4-DMD, for example, are generally between about 0.1 mg 4-DMD/kg body weight and about 5 mg/kg body weight. These dosages are contemplated as adequate in most conditions for their use in antitumor therapy of man. A more preferable dose range is between about 0.2 mg/kg and about 3 mg/kg. The particular dosages, if humans are being treated, may vary in each case according to the condition of the patient, the type and extent of the tumor and directions of an attending physician.

A focal point of the present invention involves a method of treating a host animal afflicted with tumor cells sensitive to the selected anthracycline. This method comprises administering to the host an amount of a liposome of the present invention comprising a phospholipid and a tumor cell-inhibiting effective amount of the drug. The administering step is preferably parenteral, for example, by intravenous, intraarterial, intramuscular, intralymphatic, intraperitoneal, subcutaneous, intrapleural or intrathecal injection or by topical application or oral dosage. Such administration is preferably repeated on a timed schedule, for example, every three weeks. The treatment may be maintained until the tumor cell burden has been eliminated and may be used in conjunction with other forms of cancer therapy or support therapy. Such parenteral administration preferably involves L-4-DMD, for example, suspensions in pharmaceutically acceptable solutions such as sterile isotonic aqueous solutions. These suspensions may be obtained fully prepared or may be prepared from preformed components. As known to those skilled in the art, the liposomal drug may be prepared and mixed with pharmaceutically acceptable solutions to form suspensions for parenteral administration.

The methods of preparation of liposomal anthracycline and chemotherapeutic treatment therewith described in the Examples contained later herein are readily adapted to the production and use of analogously described liposomes by simple substitutions of appropriate lipids or methods.

Liposomes containing a selected anthracycline as described herein may be prepared from various amphipathic substances including natural or synthetic phospholipids. The phospholipids usable to produce liposomes are numerous and not exhaustively listed herein since they are generally well known in the art. These phospholipids include but are not limited to: lecithin, phosphotidylglycerol, phosphotidycholine, phosphatidylethanolamine, lysolecithin, lysophatidylethanolamine, phosphatidylserine, phosphatidylinositol, sphingomyelin, cardiolipin, phosphatidic acid and the cerebrosides, with the preferred phospholipids being phosphatidylcholine, phosphatidylglycerol or a combination thereof. Most preferable phospholipids for the practice of aspects of the present invention include dimyristoylphosphatidylglycerol (DMPG) and dimyristoylphosphatidylcholine (DMPC). A sterol such as cholesterol in proportions ranging from less than 1% to about 50% may be included with phospholipids and anthracycline to produce liposomes of the present invention. A preferable but not limiting combination of DMPG and DMPC has been found to be ratio of 3 to 7 although ratios between 1:10 and 10:1 are contemplated as satisfactory.

Either unilamellar or multilamellar or other types liposomes may be used in the practice of the present invention. Multilamellar liposomes are presently preferred since the anthracyclines employed in the present invention are substantially water-insoluble. These agents appear to be incorporated into the phospholipid bilayers of the liposome lamellae.

These following examples are presented to describe preferred embodiments and utilities of the present invention but are not meant to limit the present invention. For example, although dimyristoylphosphatidylcholine and dimyristoylphosphatidylcholine were used to form liposomes, these particular lipid forms are by no means the only available usable lipids known to those skilled in the art. Nor do the particular formation methods for or types of liposomes used in these examples represent the only usable methods or liposome types. Moreover, although these examples employ the analog 4-DMD, the procedures, results and effective dose ranges should be similar for the other 4-demethoxy-3'-desamino-2'iodo anthracyclines.

EXAMPLE 1

PREPARATION OF LIPOSOMES CONTAINING 4-DMD

4-DMD was synthesized by Dr. Waldemar Priebe at the University of Texas M.D. Anderson Hospital & Tumor Institute as disclosed by U.S. Pat. No. 4,537,882, incorporated herein by reference. Chromatographically pure (by thin layer chromatography) dimyristoylphosphatidyl choline and dimyristoylphosphatidyl glycerol were purchased from Avanti Polar Lipids (Birmingham, Ala.).

Three different methods of preparation of liposomes were developed:

1. Liposomal-4-DMD suspension in aqueous solution.

Multilamellar vesicles containing 4-DMD were prepared as previously reported for other compounds (Perez-Soler et al., (1986) Cancer Research, 46:6269–6273). In brief, chloroform or methanol solutions of lipids (at the desired molar ratio) and 4-DMD were mixed at a lipid: 4-DMD ratio of 15: 1 and the organic solvent was evaporated in a rotary evaporator. The dried lipid film obtained, containing 4-DMD, was then dispersed with an aqueous solution (preferably 0.9% NaCl in water, 1 ml/mg 4-DMD) by mild handshaking. The liposomal suspension obtained was observed by optic microscopy under fluorescence. Red fluorescent multilamellar liposomes were easily identified. No drug precipitates or vesicle clumps could be seen. Liposomes were sized in Coulter Counter and Channelizer. Size ranged from 1 to 5 um, with the peak at 2 um.

2. Liposomal-4-DMD in dried powder

Method A

Dimyristoylphosphatidyl choline, dimyristoylphosphatidyl glycerol, and 4-DMD were dissolved in t-butyl alcohol (weigh ratio 10.5:4.5:1). Other organic solvents such as cyclohexane can also be used for this procedure. The solution was freeze-dried overnight. A dried red powder was obtained. Multilamellar liposomes were formed upon reconstitution of the powder with an aqueous solution (preferably 0.9% NaCl, 1 ml/mg 4-DMD). The reconstitution process required vortexing for 1 min at a temperature ranging from 25° C. to 40° C. Red fluorescent liposomes were seen by light microscopy, no precipitates of drug or vesicle clumps were identified. Liposome size ranged between 1 and 3 um, with the peak at 2 um.

Method B

A suspension of liposomal-4-DMD as described above (liposomal-4-DMD suspension in aqueous solution) was prepared using distilled water instead of 0.9%

NaCl in water. Red fluorescent liposomes were seen by light microscopy. No drug precipitates or vesicle clumps were observed. The suspension was freeze-dried overnight. A dried red powder was obtained. Multilamellar liposomes were formed upon reconstitution of the powder with an aqueous solution (preferably 0.9% NaCl, 1 ml/mg 4-DMD). The reconstitution process required vortexing for 1 min at a temperature ranging from 25° C. to 40° C. Red fluorescent liposomes were seen by light microscopy, no precipitates of drug or vesicle clumps were identified. Liposome size ranged between 1 and 3 um, with the peak at 2 um.

EXAMPLE 2

ENCAPSULATION EFFICIENCY AND STABILITY OF LIPOSOMAL-4-DMD

The encapsulation efficiency of liposomal-4-DMD was assessed by measuring the amount of 4-DMD bound to the lipid phase and in the aqueous phase. The liposomal suspension was centrifuged at 30,000 x g for 45 min at 4° C. A red pellet and a clear supernatant were obtained. 4-DMD was measured both in the supernatant and the pellet by UV spectrophotometry at a wavelength of 250 nm. The encapsulation efficiency was calculated using the following formulas:
1. % Encapsulation efficiency=4-DMD in pellet/4-DMD added×100
2. % Encapsulation efficiency=4-DMD added - 4-DMD in supernatant/4-DMD added×100

The encapsulation efficiency was in all cases greater than 95%. See Table I below. No differences in encapsulation efficiency were observed between the different types of liposome preparation, as described in Example 1. In addition, the pellets were observed by light microscopy under fluorescence to rule out the presence of drug precipitates in the space around the vesicles. No drug precipitates were seen in any case.

The vesicle stability was assessed by measuring the amount of 4-DMD associated with the aqueous phase 3 weeks after the preparation of liposomal-4-DMD in suspension prepared by any of the methods described in Example 1. The suspensions were kept at 4° C. An excess of 95% of 4-DMD was still bound to the lipid phase at 3 weeks and no drug precipitates were observed by optic microscopy under fluorescence. See Table I below. The liposomes containing 4-DMD still appeared homogeneously spherical with a typical multilamellar structure.

TABLE I

| ENTRAPMENT AND STABILITY OF LIPOSOMAL-4-DMD | |
| --- | --- |
| Entrapment efficiency | >95% |
| 3 weeks stability in normal saline | >95% |

EXAMPLE 3

SUBACUTE TOXICITY OF LIPOSOMAL-4-DMD IN MICE

Groups of 6 CD-1 mice each were injected intravenously with different doses of liposomal-4-DMD or doxorubicin ranging from 10 to 25 mg/kg. Animals were observed and deaths up to day 14 recorded. The $LD_{10}$ of liposomal-4-DMD was greater than 25 mg/kg (highest dose tested) while the $LD_{50}$ of doxorubicin was 22 mg/kg. See Table II below.

TABLE II

| SUBACUTE TOXICITY OF LIPOSOMAL 4-DMD | | | |
| --- | --- | --- | --- |
| Drug | $LD_{10}$ mg/Kg | $LD_{50}$ mg/kg | $LD_{90}$ mg/kg |
| Doxorubicin | 20.5 | 22 | >25 |
| Liposomal-4-DMD | >25 | >25 | >25 |

EXAMPLE 4

ANTITUMOR ACTIVITY OF LIPOSOMAL-4-DMD AGAINST L1210 LEUKEMIA

The antitumor activity of liposomal-4-DMD was tested in the L1210 mouse leukemia model and compared with that of doxorubicin. $1\times10^6$ L1210 cells were inoculated ip on day 0 to male BDF1 mice weighing 20–22 g. Treatment was administered ip on day 1 or days 1, 5 and 9. Survival of the animals was monitored on a daily basis. Results were expressed at % T/C (median survival of treated animals/median survival of control animals×100). Doxorubicin at the previously reported optimal dose resulted in a % T/C of 212 and 187 for the single and the triple dose schedule, respectively. No animals were cured. Liposomal-4-DMD was clearly superior with a % T/C greater than 600 for both schedules, and a cure rate of 80% and 50%, respectively.

Liposomal-4-DMD was much more potent than doxorubicin, particularly when given in a triple dose schedule, with the optimal total dose being 4 times lower than that of doxorubicin. See Table III below.

TABLE III

| ANTITUMOR ACTIVITY OF LIPOSOMAL-4-DMD AGAINST L-1210 LEUKEMIA | | | | |
| --- | --- | --- | --- | --- |
| Drug | Schedule day | Route | Dose mg/kg | % T/C (% cured) |
| Doxorubicin | 1 | i.p. | 10 | 212 (0) |
| Liposomal-4-DMD | 1 | i.p | 12.5 | >600 (80) |
| Doxorubicin | 1, 5, 9 | i.p. | 8 | 187 (0) |
| Liposomal-4-DMD | 1, 5, 9 | i.p. | 2 | >775 (50) |

EXAMPLE 5

ANTITUMOR ACTIVITY OF LIPOSOMAL-4-DMD AGAINST LIVER METASTASES OF MOUSE M5076 RETICULOSARCOMA

The antitumor activity of liposomal-4-DMD was also tested against established experimental liver metastases of M5076 reticulosarcoma. $2\times10^4$ M5076 cells were inoculated i.v. on day 0 to male C57BL/6 mice weighing 20–22 g. Treatment with doxorubicin or liposomal-4-DMD was administered i.v. on days 4 or days 4, 8, and 12. The doses of doxorubicin used were the optimal as previously reported. Survival of the animals was monitored on a daily basis. Results were expressed as % T/C. Doxorubicin at the optimal dose was not active when given as a single dose and barely active when the triple dose schedule was used (% T/C 133). On the other hand, liposomal-4-DMD had significant activity when given as a single dose (% T/C 172), and the activity was enhanced by the triple dose schedule (% T/C 200). With the i.v. route, liposomal-4-DMD was also much more potent than doxorubicin, the optimal total dose for the triple schedule being about three times lower than that of doxorubicin. See Table IV below.

ANTITUMOR ACTIVITY OF
LIPOSOMAL-4-DMD AGAINST LIVER
METASTASES OF M5076 RETICULOSARCOMA

| Drug | Schedule day | Route | Dose mg/kg | % T/C |
|---|---|---|---|---|
| Doxorubicin | 4 | i.v. | 10 | 109 |
| Liposomal-4-DMD | 4 | i.v. | 12.5 | 172 |
| Doxorubicin | 4, 8, 12 | i.v. | 8 | 133 |
| Liposomal-4-DMD | 4, 8, 12 | i.v. | 3.1 | 200 |

What is claimed is:

1. A composition comprising liposomal vesicles having incorporated therein a 4-demethoxy-3'-desamino-2'-iodo anthracycline analog.

2. The composition of claim 1 wherein the anthracycline analog is selected from compounds of the formula:

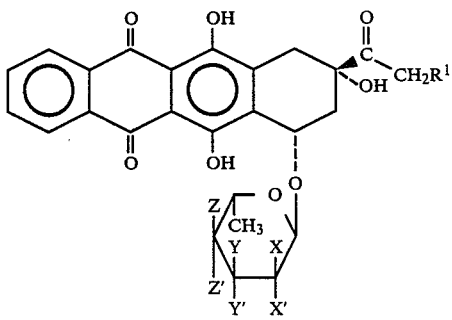

wherein $R^1$ is hydroxy; one of X and X' is hydrogen and the other is iodine; one of Y and Y' is hydrogen and the other is hydroxy; one of Z and Z' is hydrogen and the other is hydroxy.

3. The composition of claim 2 wherein said compound is 4-demethoxy-7-O-(2-iodo-2,6-dideoxy-alpha-L-mannohexopyranosyl)adriamycinone.

4. The composition of claim 1 wherein said liposomal vesicles are dispersed in a pharmaceutically acceptable aqueous diluent.

5. The composition of claim 1 comprising a ratio of incorporated anthracycline to lipid of between about 1:5 to about 1:50.

6. The composition of claim 5 wherein the incorporated anthracycline to lipid ratio is about 1:15.

7. The composition of claim 1 wherein the liposomal vesicles include one or more of phosphomonoglyceride, phosphatidic acid and sphingolipid.

8. The composition agent of claim 1 wherein the liposomal vesicles include one or more of phosphatidylcholine, phosphatidylserine, phosphatidylglycerol, sphingomyelin and phosphatidic acid.

9. The composition of claim 1 wherein the liposomal vesicles include one or more of dimyristoylphosphatidylcholine, dimyristoylphosphatidylglycerol, phosphatidylcholine and phosphatidylglycerol.

10. The composition of claim 1 wherein the liposomal vesicles consist essentially of dimyristoylphosphatidylcholine and dimyristoylphosphatidylglycerol.

11. The composition of claim 10 wherein the liposomal vesicles are defined further as consisting essentially of dimyristoylphosphatidycholine and dimyristoylphosphatidylglycerol in a ratio of between about 1 to 10 and about 10 to 1.

12. The composition of claim 1 wherein the liposomal vesicles consist essentially of dimyristoylphosphatidylcholine and dimyristoylphosphatidylglycerol in a ratio of about 7:3.

13. The composition of claim 1 wherein the liposomal vesicles are defined further as being stable multilamellar vesicles.

14. The composition of claim 1 wherein the liposomal vesicles are defined further as comprising a sterol.

15. The composition of claim 14 wherein the sterol is cholesterol.

16. The composition of claim 1 in the form of a dried powder.

17. A process for preparing an improved anthracycline containing composition comprising:
(a) selecting n anthracycline analog from compounds having the formula:

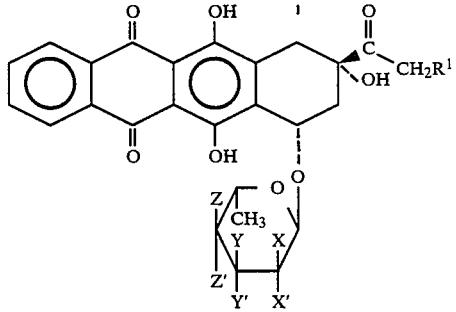

wherein $R^1$ is hydroxy; one of X and X' is hydrogen and the other is iodine; one of Y and Y' is hydrogen and the other is hydroxy; one of Z and Z' is hydrogen and the other is hydroxy; and
(b) incorporating said anthracycline analog with lipids.

18. The method of claim 17 wherein step (b) comprises forming liposomes.

19. The method of claim 17 further comprising drying the anthracycline and lipids to form a powder.

20. The method of claim 18 further comprising drying the anthracycline-incorporated liposomes to form a powder.

21. The method of claim 19 or 20 further comprising hydrating the dried powder with a pharmaceutically acceptable diluent.

22. A method of treating cancer in a patient comprising administering to the patient an effective dose of a composition according to any one of claims 1 through 16.

UNITED STATES PATENT AND TRADEMARK OFFICE
CERTIFICATE OF CORRECTION

PATENT NO. : 4,863,739
DATED     : September 5, 1989
INVENTOR(S) : Perez-Soler et al.

It is certified that error appears in the above—identified patent and that said Letters Patent is hereby corrected as shown below:

Column 10, line 24, please delete --n-- and insert therefor "an".

Signed and Sealed this

Sixth Day of April, 1993

Attest:

STEPHEN G. KUNIN

*Attesting Officer*      Acting Commissioner of Patents and Trademarks